(12) United States Patent
Bilotti et al.

(10) Patent No.: US 8,646,673 B2
(45) Date of Patent: *Feb. 11, 2014

(54) SURGICAL STAPLING INSTRUMENT

(75) Inventors: Federico Bilotti, Rome (IT); Antonio Longo, Palermo (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 572 days.

This patent is subject to a terminal disclaimer.

(21) Appl. No.: 12/830,010

(22) Filed: Jul. 2, 2010

(65) Prior Publication Data
US 2010/0308101 A1   Dec. 9, 2010

Related U.S. Application Data

(63) Continuation of application No. 11/362,405, filed on Feb. 24, 2006, now abandoned, which is a continuation of application No. 10/869,103, filed on Jun. 14, 2004, now abandoned, which is a continuation of application No. 10/287,066, filed on Nov. 4, 2002, now Pat. No. 6,805,273, which is a continuation-in-part of application No. PCT/EP01/03615, filed on Mar. 29, 2001.

(51) Int. Cl.
*A61B 17/072* (2006.01)

(52) U.S. Cl.
USPC ............... 227/175.1; 227/19; 227/176.1

(58) Field of Classification Search
USPC ............ 227/19, 175.1, 176.1, 180.1; 606/219
See application file for complete search history.

(56) References Cited

U.S. PATENT DOCUMENTS

| | | |
|---|---|---|
| 3,692,224 A | 9/1972 | Astafiev et al. |
| 4,354,628 A | 10/1982 | Green |
| 4,485,811 A | 12/1984 | Chernousov et al. |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,566,620 A | 1/1986 | Green et al. |

(Continued)

FOREIGN PATENT DOCUMENTS

| EP | 0213817 A1 | 3/1987 |
|---|---|---|
| EP | 0373823 A2 | 6/1990 |

(Continued)

OTHER PUBLICATIONS

Transanal Endoscopic Surgery of the Rectum, 1985.

*Primary Examiner* — Alexandra Elve
*Assistant Examiner* — Nathaniel Chukwurah

(57) ABSTRACT

A surgical stapling instrument (1) comprises a body portion (2, 3), a handle (4) and a staple fastening assembly (8). The staple fastening assembly (8) includes a curved cartridge (10), which comprises at least one curved open row of staples, and a curved anvil (22), which is adapted to cooperate with the cartridge (10) for forming the ends of the staples exiting from the cartridge (10). The staple fastening assembly (8) is adapted to allow unobstructed access towards the concave inner faces of the cartridge (10) and the anvil (22). The cartridge (10) can be moved towards the anvil (22) from a spaced position for positioning tissue therebetween to a closed position for clamping the tissue. Preferably, a knife is contained within the cartridge (10) and is positioned such that there is at least one row of staples on at least one side of the knife.

1 Claim, 8 Drawing Sheets

(56) References Cited

U.S. PATENT DOCUMENTS

Figure 1:
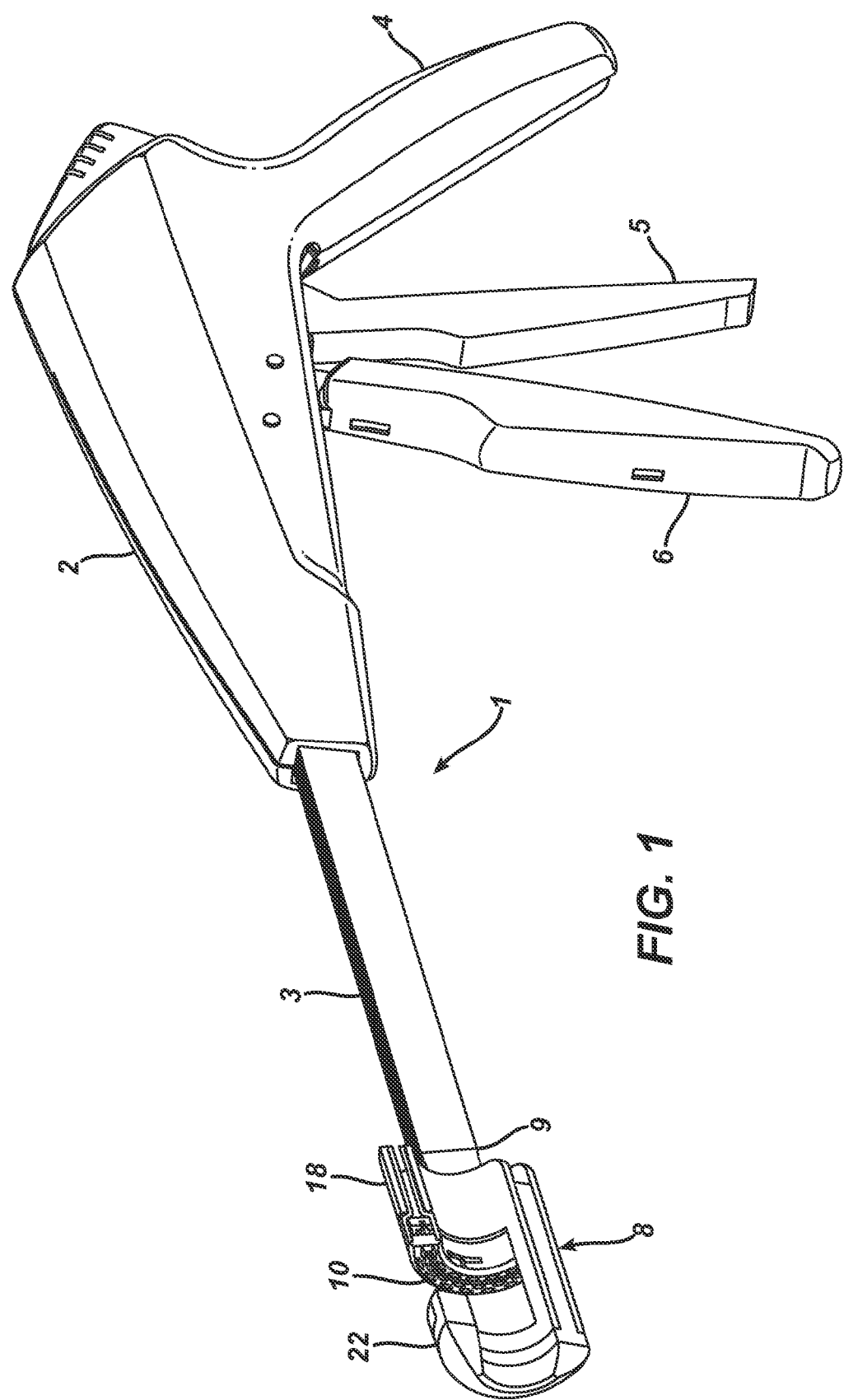

| | | |
|---|---|---|
| 4,568,009 A | 2/1986 | Green |
| 4,580,712 A | 4/1986 | Green |
| 4,617,928 A | 10/1986 | Alfranca |
| 4,665,916 A | 5/1987 | Green |
| 4,684,051 A | 8/1987 | Akopov et al. |
| 4,715,520 A | 12/1987 | Roehr, Jr. et al. |
| 4,728,020 A | 3/1988 | Green et al. |
| 4,788,978 A | 12/1988 | Strekopytov et al. |
| 4,802,614 A | 2/1989 | Green et al. |
| 4,819,853 A | 4/1989 | Green |
| 4,869,414 A | 9/1989 | Green et al. |
| 4,881,545 A | 11/1989 | Isaacs et al. |
| 4,892,244 A | 1/1990 | Fox et al. |
| 5,100,042 A | 3/1992 | Gravener et al. |
| 5,116,349 A | 5/1992 | Aranyi |
| 5,129,570 A | 7/1992 | Schulze et al. |
| 5,137,198 A | 8/1992 | Nobis et al. |
| 5,156,315 A | 10/1992 | Green et al. |
| 5,156,614 A | 10/1992 | Green et al. |
| 5,163,957 A | 11/1992 | Sade et al. |
| 5,190,203 A | 3/1993 | Rodak |
| 5,275,323 A | 1/1994 | Schulze et al. |
| 5,344,060 A | 9/1994 | Gravener et al. |
| 5,352,238 A | 10/1994 | Green et al. |
| 5,355,897 A | 10/1994 | Pietrafitta et al. |
| 5,360,154 A | 11/1994 | Green |
| 5,368,599 A | 11/1994 | Hirsch et al. |
| 5,379,933 A | 1/1995 | Green et al. |
| 5,389,098 A | 2/1995 | Tsuruta et al. |
| 5,395,030 A | 3/1995 | Kuramoto et al. |
| 5,413,267 A | 5/1995 | Solyntjes et al. |
| 5,439,155 A | 8/1995 | Viola |
| 5,458,279 A | 10/1995 | Plyley |
| 5,462,215 A | 10/1995 | Viola et al. |
| 5,470,006 A | 11/1995 | Rodak |
| 5,470,008 A | 11/1995 | Rodak |
| 5,470,009 A | 11/1995 | Rodak |
| 5,509,596 A | 4/1996 | Green et al. |
| 5,551,622 A | 9/1996 | Yoon |
| 5,558,266 A | 9/1996 | Green et al. |
| 5,579,978 A | 12/1996 | Green et al. |
| 5,605,272 A | 2/1997 | Witt et al. |
| 5,615,820 A | 4/1997 | Viola |
| 5,641,111 A | 6/1997 | Ahrens et al. |
| 5,653,373 A | 8/1997 | Green et al. |
| 5,655,698 A | 8/1997 | Yoon |
| 5,662,259 A | 9/1997 | Yoon |
| 5,662,260 A | 9/1997 | Yoon |
| 5,697,543 A | 12/1997 | Burdorff |
| 5,706,998 A | 1/1998 | Plyley et al. |
| 5,735,445 A | 4/1998 | Vidal et al. |
| 5,810,240 A | 9/1998 | Robertson |
| 5,833,695 A | 11/1998 | Yoon |
| 5,868,760 A | 2/1999 | McGuckin, Jr. |
| 5,878,937 A | 3/1999 | Green et al. |
| 6,119,913 A | 9/2000 | Adams et al. |
| 6,126,058 A | 10/2000 | Adams et al. |
| 6,179,195 B1 | 1/2001 | Adams et al. |
| 6,241,140 B1 | 6/2001 | Adams et al. |
| 6,264,086 B1 | 7/2001 | McGuckin, Jr. |
| 6,264,088 B1 | 7/2001 | Larsson |
| 6,343,731 B1 | 2/2002 | Adams et al. |
| 6,805,273 B2 * | 10/2004 | Bilotti et al. ............... 227/180.1 |
| 2002/0047036 A1 | 4/2002 | Sullivan et al. |

FOREIGN PATENT DOCUMENTS

| | | |
|---|---|---|
| EP | 0323016 B1 | 2/1994 |
| EP | 0446012 B1 | 1/1996 |
| WO | WO 97/47231 A2 | 12/1997 |
| WO | WO 01/91646 A1 | 12/2001 |
| WO | WO 02/30296 A2 | 4/2002 |

* cited by examiner

SURGICAL STAPLING INSTRUMENT

CROSS-REFERENCE TO RELATED APPLICATIONS

This Continuation Application claims priority to and incorporates by reference co-pending and commonly assigned U.S. Ser. No. 11/362,405 filed Feb. 24, 2006, now abandoned which is continuation of U.S. Ser. No. 10/869,103 filed Jun. 14, 2004 (now abandoned); which is a continuation of U.S. Ser. No. 10/287,066 filed Nov. 4, 2002 (now U.S. Pat. No. 6,805,273); which is a Continuation-In-Part of U.S. application PCT/EP01/03615 filed on Mar. 29, 2001.

FIELD OF THE INVENTION

The invention relates to a surgical stapling instrument, which can be used, e.g., in the diagnosis and therapy of all pathologies best treated by a curved stapled resection. It provides a means to extend the transluminal exploitation of mechanical suturing devices introduced via the anal canal, mouth, stomas, and service accesses. The treatment of rectal pathologies will be described as most frequent, but not only use of the invention.

The current transanal surgical procedure of choice is Transanal Endoscopic Microsurgery, which, however is burdened with difficulty of execution and complications such as dehiscence and abscesses. Current endoscopic excisions of, e.g., peduncular polyps usually do not allow necessary histological examination. This is of particular concern when the sample turns out to be malignant and the site is no longer visible during follow-up surgery. In the case of sessile polyps, the endoscopic excision presents similar drawbacks, and in addition difficulties in retrieving the sample, a related high loss of blood, and a risk of perforation of the intestinal wall. Traditional surgical excisions, for example via Transanal Endoscopic Microsurgery, are complicated and involve the intraluminal dissemination of neoplastic cells.

WO 97/47231 discloses an endoscopic stapler including a stapling head which is removably located on the distal end of an endoscope. The stapling head includes a stationary part, which houses a removable staple cartridge, and a movable part which includes an anvil for receiving and bending the ends of staples fired from the staple cartridge. The stationary part has a circular cross-sectional area, but the staples are arranged in two semi-circular rows, in which the staples are staggered relative to each other. The cross-sectional shape of the anvil is semi-circular, generally matching the rows of staples. After tissue to be excised has been clamped by moving the anvil towards the stationary part, the staples are consecutively expelled from the staple cartridge, and a knife cuts the tissue to be excised by moving along a staple line. Since the access for manipulating the tissue in order to place it correctly in between the anvil and the stationary part is somewhat obstructed by the cross-sectional shape of the stationary part, a remote-controlled forceps device is provided in the region of the staples and the anvil.

In U.S. Pat. No. 5,355,897, a surgical stapler is shown which derives from the well-known circular staplers for performing an anastomosis. In order to enable the local excision of tissue by means of this instrument, instead of a circular anastomosis, a shield extending around part of the periphery of the stapling region prevents unwanted tissue from entering the head of the device. A similar instrument is known from U.S. Pat. No. 5,360,154. In both cases, the region between the anvil and the staple cartridge is not easily accessible.

Surgical staplers comprising a staple cartridge having one or more straight rows of staples and a cutting blade running in parallel to the staples are disclosed in U.S. Pat. Nos. 4,665,916 and 4,881,545. In these instruments, tissue to be stapled and excised can be clamped between the staple cartridge and an anvil which is pivotally connected to the staple cartridge at one of its ends. Staplers having straight rows of staples, in which the staple cartridge can be moved in parallel relationship with respect to a stationary anvil in order to clamp the tissue to be stapled and excised, are known from U.S. Pat. Nos. 4,527,724, 5,137,198, and 5,605,272; these staplers are not provided with an automated cutting device. Generally, in many applications, straight staplers are not anatomically correct, i.e. straight staple lines do not fit a circular lumen contour.

U.S. Pat. No. 4,617,928 discloses a surgical instrument for practising mechanical sutures and biopsies. This instrument comprises a fixed anvil and a staple cartridge (including a knife), which can be moved towards the anvil in order to clamp tissue between the anvil and the staple cartridge. In one embodiment, there are two staple rows arranged in a V-shaped configuration around a V-shaped knife. In another embodiment, an approximately semi-circular double row of staples surrounds an approximately semi-circular knife. In this embodiment, which is designed for practising pulmonary biopsies, free access to the inner faces of the cartridge and the anvil is hindered by an arm supporting the cartridge.

The object of the present invention is to provide an economical surgical stapling instrument for stapling (and optionally resecting) tissue, in particular inside the digestive track, which can be operated and used in a safe, effective, and fast manner.

This problem is solved by a surgical stapling instrument having the features of claim 1. Advantageous versions of the invention follow from the dependent claims.

The surgical stapling instrument according to the invention comprises a frame having a body portion and a handle extending from the body portion in the proximal end region of the instrument. A staple fastening assembly is mounted in the distal end region of the instrument. Here and in the following, the terms "proximal" and "distal" relate to the user as reference, which means that the parts of the instrument close to the user under normal operating conditions are designated as "proximal".

The staple fastening assembly includes a curved cartridge, which comprises at least one curved open row of staples, and, at the distal end of the instrument, a curved anvil, which is adapted to cooperate with the cartridge for forming the ends of the staples exiting from the cartridge. The staple forming plane of the anvil is arranged transversally with respect to the longitudinal axis of the body portion of the instrument. The staple fastening assembly is adapted to allow unobstructed access towards the concave inner faces of the cartridge and the anvil and thus to the tissue to be resected.

A cartridge moving device is adapted to move the cartridge essentially in parallel relationship towards the anvil from a spaced position for positioning tissue therebetween to a closed position for clamping the tissue. The staples can be driven out of the cartridge towards the anvil by means of a staple driving device.

Herein, the term "staple" is used in a very general sense. It includes metal staples or clips, but also surgical fasteners made of synthetic material and similar fasteners. Synthetic fasteners usually have a counterpart (retainer member) held at the anvil. In this sense, the terms "anvil" and "staple forming plane" also have a broad meaning which includes, in the case of two-part synthetic fasteners, the anvil-like tool and its plane where the retainer members are held, and similar devices.

Preferably, a knife is contained within the cartridge and is positioned such that there is at least one row of staples on at least one side of the knife. The knife is moved towards the anvil by means of a knife actuating device. If the stapling instrument does not include a knife, tissue to be resected after stapling can be cut by means of a separate surgical instrument.

The main advantage of the surgical stapling instrument according to the invention is its ability to allow endoluminal tissue resections and stapling through direct vision. Additionally, separate optics (e.g., an endoscope) can be used as an option. When the instrument is introduced into, e.g., the anal canal, free view onto and access to the site of the tissue to be resected is not obstructed by any parts of the instrument. The tissue to be excised can be pulled into the area in between the anvil and the cartridge, when the cartridge is in a spaced or open position, by means of a separate gripping instrument. Because of the unobstructed access towards the concave inner faces of the cartridge and the anvil, the gripping instrument can be used easily, effectively and safely. Afterwards, the cartridge is moved towards the anvil in order to clamp the tissue. A particular advantage is that the surgeon can well observe the clamping procedure when the movable cartridge approaches the resting anvil. When the cartridge has reached the closed position, the surgeon can "fire" the instrument, which means that the staples are driven out of the cartridge, penetrate the tissue, whereupon their ends are bent by the anvil, and the knife is moved towards the anvil in order to cut the tissue. When the instrument is retracted, the completely excised tissue stays in the staple fastening assembly and can thus be safely removed from the patient's body.

The surgical stapling instrument according to the invention allows, e.g., the removal of a peduncular polyp and surrounding mucosa for optimal histological examination. Moreover, a valuable trace in the form of staples is left in the patient's body which allows to find the site of the operation at a later time easily if a subsequent examination is required. In the case of sessile polyps, the advantages of the instrument are the rapid deployment of sterile sealing means (i.e. staples) and a low blood loss. Optimal histological examination results are possible because a good definition of possible muscular and perirectal infiltration of neoplastic cells is allowed. In the case of benign polyps and early diagnosed rectal cancer, the surgical procedure can be considered curative.

Examples for other applications of the surgical stapling instrument according to the invention are the treatment of mucosa prolapses of the rectum, rectoceles, anterior prolapses of the rectum, rectal prolapses, rectal ulcers, stenoses (e.g., at an anastomic site), Meckel diverticulum, esophageal pathologies, the transrectal stapling of trauma wounds, the intussusception of the rectum, and the resection of polyps via service enterotomy.

Preferably, the outer faces of the cartridge and the anvil are ergonomically shaped to match the anatomy of the internal lumen of the digestive track. The cartridge and the anvil can have a generally arc-like shape in the cross-sectional plane, the arc extending over an angle in the range 90° to 270°.

In an advantageous version, the staple fastening assembly includes a curved guide portion, wherein the cartridge is mounted for movement between the distal end of the guide portion and the anvil. Preferably, the shape of the guide portion is arc-like in the cross-sectional plane and is similar to that of the cartridge and the anvil, allowing an unobstructed access towards the concave inner face of the guide portion as well. Preferably, the guide portion and the anvil are rigidly connected by means of at least one arm extending from at least one end of the anvil and generally running in parallel to the longitudinal axis of the body portion of the instrument. This arm does not interfere with surgical instruments used for manipulating the tissue to be excised and does not block the surgeon's view. A staple fastening assembly designed in this way greatly facilitates the surgical applications of the instrument.

In an advantageous embodiment, there is at least one row of staples on each side of the knife. The advantage of this arrangement is that the tissue is safely held on both sides of the knife when the knife cuts the tissue, thus ensuring a clean excision of the tissue. Another advantage is that hemostasis of the resected site is maintained during the procedure. The staples sticking in the excised tissue are removed from the patent's body together with that tissue specimen.

The distance between the cartridge and the anvil in the closed position is preferably adjustable. For example, the cartridge moving device can comprise an adjustable stop in order to prevent the cartridge from moving beyond the stop position and from clamping the tissue too much. Or a series of cartridges with different built-in tissue stops can be used according to the tissue thickness. It is also conceivable to use a series of cartridges which have different longitudinal dimensions which are adapted to the desired distance between the cartridge and the anvil in the closed position. By adjusting the distance between the cartridge and the anvil in the closed position, the instrument can be matched to the thickness and type of tissue to be excised.

In an advantageous version, the staple driving device is adapted to simultaneously drive the staples out of the cartridge towards the anvil, and the knife actuating device is adapted to cause the knife to protrude from the cartridge after the staple points have been driven out of the cartridge. In this design, pre-ferably the staple driving device and the knife actuating device are mechanically coupled for operation via a common trigger. This way of controlling the operation of the staples and the knife ensures a well-defined and clean cutting line in the tissue, while the handling is easy.

Preferably, the cartridge is removable so that a used cartridge without staples can be replaced with a fresh one, if required. This is particularly advantageous if the instrument is to be used several times during the same surgical procedure. It is also conceivable to design the instrument as a re-usable instrument which is sterilized after each surgical procedure. In this case, a fresh and sterile cartridge can be inserted during the next surgical procedure.

When the cartridge is removable, it can be mounted, e.g., in a cartridge holder which embraces the cartridge along the periphery of an arc-like shape in the cross-sectional plane. This design still allows an unobstructed access towards the concave inner face of the cartridge, i.e. up to the concave inner face of the cartridge holder, which matches the shape of the cartridge in the cross-sectional plane.

In another advantageous version, the knife is removable. This allows the selection of a knife of given dimensions or cutting properties, which is optimized to the surgical procedure in question, e.g., to the timing required when the staples penetrate the tissue and the tissue is cut, or simply a replacement of the knife if desired.

Preferably, the cartridge moving device includes a trigger lever (preferably close to the handle) for actuating the movement of the cartridge. Alternatively, the cartridge moving device can include a threaded shaft which is mounted in the body portion and coupled to a rotatable knob. In this case, the longitudinal movement of the cartridge for approaching the anvil is activated by rotating the knob. Mechanisms for effecting these kinds of movements are generally known in the prior art, see, e.g., U.S. Pat. No. 4,527,724.

Preferably, the anvil has an atraumatically shaped distal end region, which facilitates, e.g., the insertion of the instrument into the rectum and the advancement of the instrument inside the lumen.

In an advantageous embodiment of the invention, the staple fastening assembly is removably mounted in the distal end region of the body portion. This allows the frame of the instrument and many parts of the cartridge moving device, the staple driving device and the knife actuating device to be designed as re-usable components, which are sterilized after each surgical procedure, whereas the staple fastening assembly can be replaced after each surgical procedure.

In the following, some advantages of the surgical stapling instrument according to the invention are summarized: It is possible to perform a surgical procedure under local anaesthetics or spinal sedation. Generally, the procedures are fast and relatively easy. The blood loss tends to be low. It is possible to apply sterile staples in a septic field, which reduces the incidence of dehiscence and abscesses. Tumors with a diameter of up to about 3 cm can be excised. It is possible to identify the type of locally advanced tumors and to determine the tumor "T" level because the tumor site is visible when the instrument is used and the excised tissue can be safely removed by means of the instrument for pathological examination. Moreover, possible mucosa or muscular infiltration can be identified (in the case of lower carcinomas, the infiltration stage is a useful tool in the decision to proceed with anterior resection or amputation). The surgical site where the staples have been left behind can be quickly identified, e.g., by using X-rays. The instrument provides the ability to remove advanced growing or stenotic rectal neoplasias via a minimal invasive approach in poor condition patients for which a radical procedure is not indicated. It is also conceivable to use the instrument as a suturing device after the completion of a transanal endoscopic microsurgery.

Moreover, the instrument can be used as a distal stump suturing device in the lower anterior resection when a double stapling technique is performed. To this end, the instrument allows rectal stump closure with the instrument introduced via a laparoscopic approach. The instrument also allows an improved rectal stump closure, which is useful because it eliminates the "Dog Ears" effect after colorectal anastomosis. Finally, the instrument allows the sealing of the specimen with a line of staples.

The surgical stapling instrument according to the invention can be even used for the excision of tumors larger than 3 cm. In this case, tissue wall mobilization is required, which can be achieved via a laparoscopic approach, via an anterior perineal access for the anterior wall, or via a posterior perineal access for the posterior wall and multiple applications of the reloadable device (i.e. of the instrument having the cartridge replaced after each firing of staples out of several actuations).

In the following, the invention is described in more detail by means of an embodiment. The drawings show in FIG. 1 an isometric view of an embodiment of the surgical stapling instrument according to the invention, which includes a frame and a staple fastening assembly with a cartridge and an anvil, the cartridge being spaced from the anvil, FIG. 2 an isometric view of the instrument after moving the cartridge into a closed position, FIG. 3 an isometric view of the instrument after firing the staples, FIG. 4 a magnified isometric view of the staple fastening assembly of the instrument, the cartridge being unlocked from the cartridge holder, FIG. 5 a view as in FIG. 4 with the cartridge fully inserted, FIG. 6 an isometric view onto the staple forming surface of the anvil of the instrument, FIG. 7 an isometric view of the cartridge of the instrument, FIG. 8 a longitudinal section through the staple fastening assembly along the line V-V in FIG. 5 after moving the cartridge into a closed position, but before firing the staples, FIG. 9 a longitudinal section as in FIG. 8, but after firing the staples and cutting the tissue, and FIG. 10 a schematic isometric view of the use of the instrument for removing a polyp in a patient's rectum.

FIG. 1 illustrates a preferred embodiment of a surgical stapling instrument 1. The instrument 1 has a frame comprising a body portion, which includes a proximal section 2 and a shaft 3, and a handle 4. The handle 4 extends from the proximal end region of the body portion and is close to a lever 5 and a trigger 6 for actuating the instrument 1, as explained below in more detail. Whereas the proximal section 2, the handle 4, the lever 5, and the trigger 6 are ergonomically shaped for facilitating the handling and manipulation of the instrument 1, the shaft 3 has a small cross-sectional area so that it does not block a surgeon's view onto a staple fastening assembly 8, which is mounted at the distal end 9 of the shaft 3, and provides sufficient support for the distal end region of the instrument.

Figure 2:
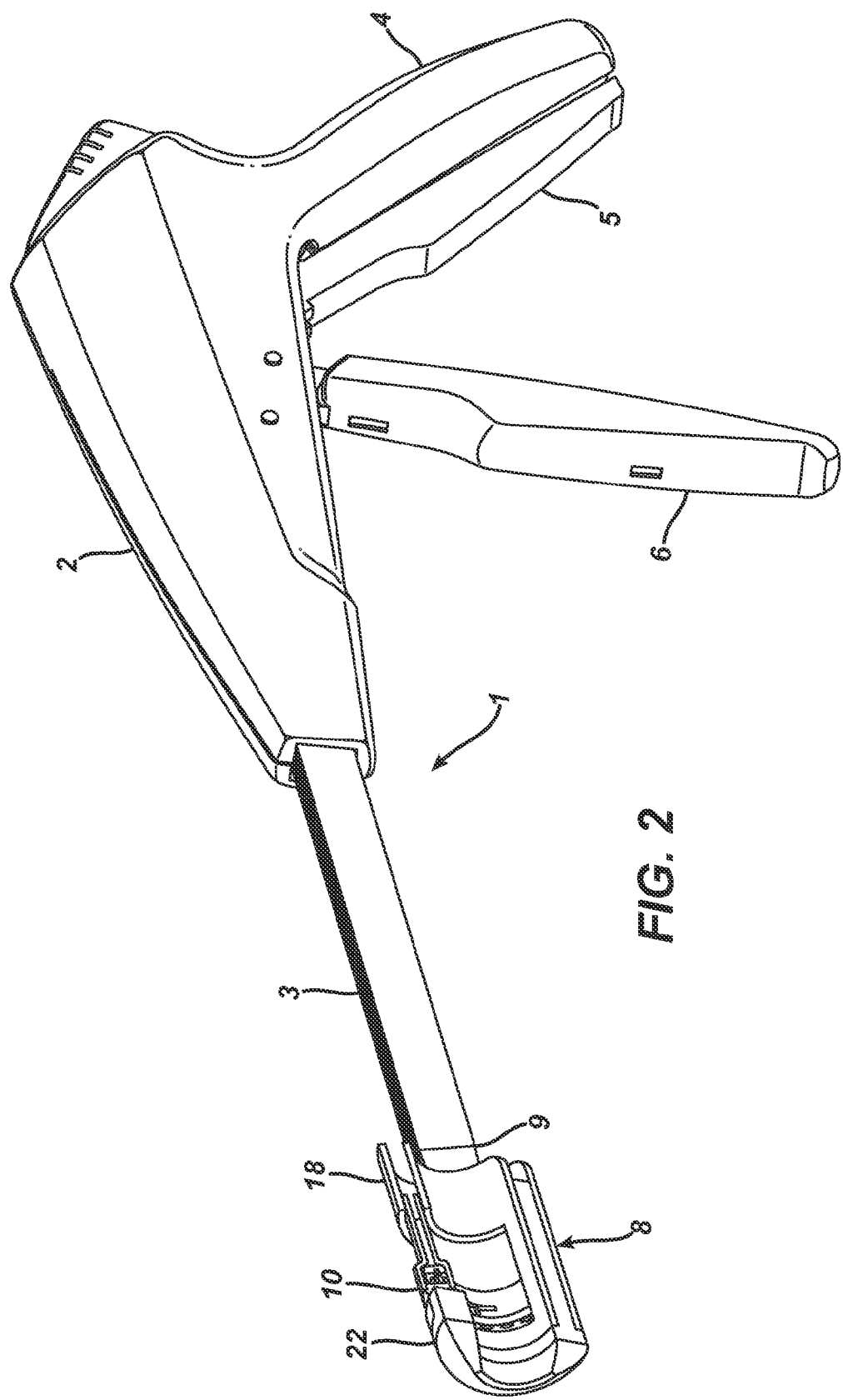
Figure 3:
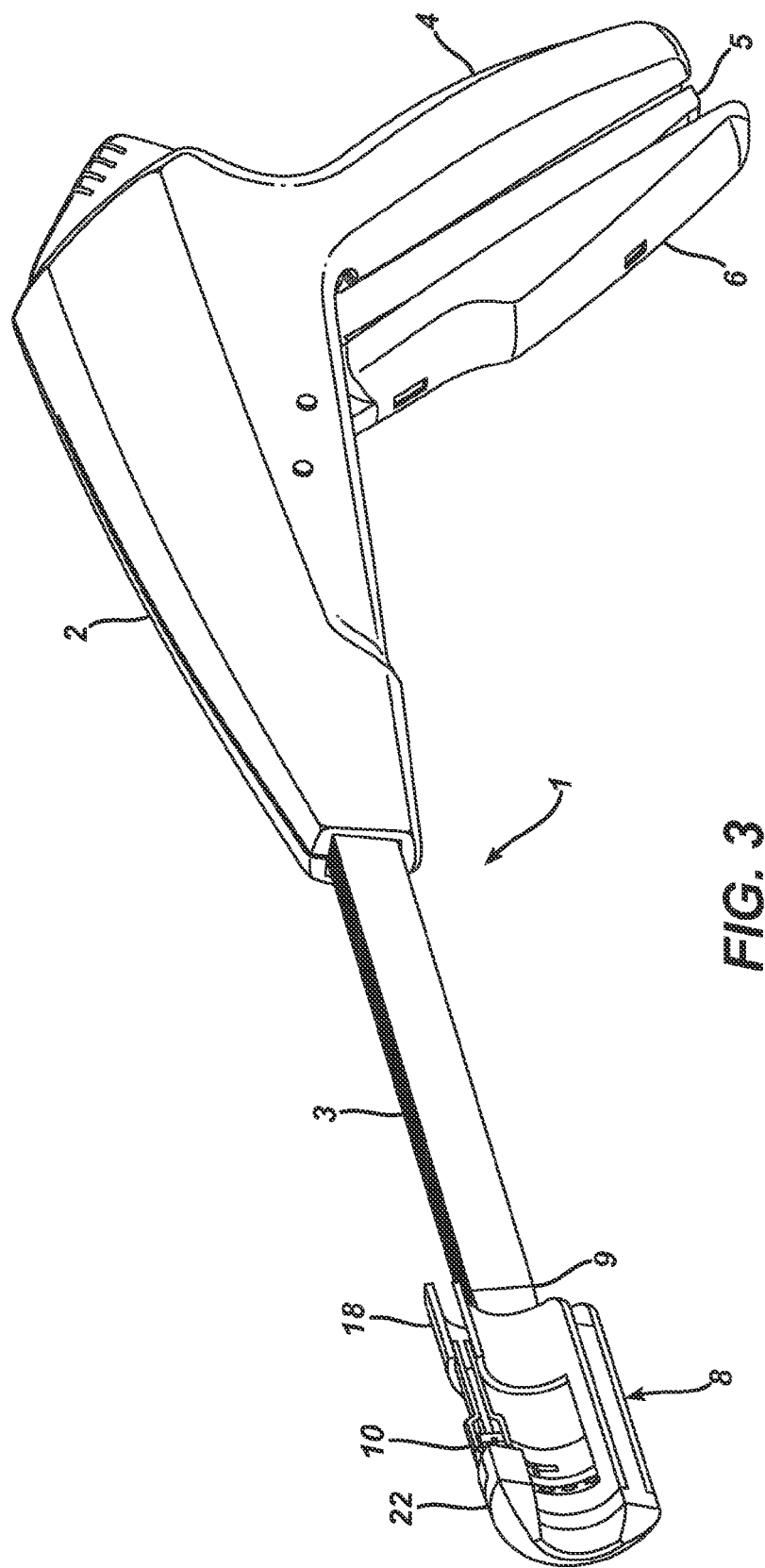

FIG. 1, FIG. 2, and FIG. 3 show the instrument 1 in three different operating states which can be achieved by actuating (i.e. turning towards the handle 4) the lever 5 and the trigger 6, respectively. The details of the different states of the staple fastening assembly 8 are explained below.

Figure 4:
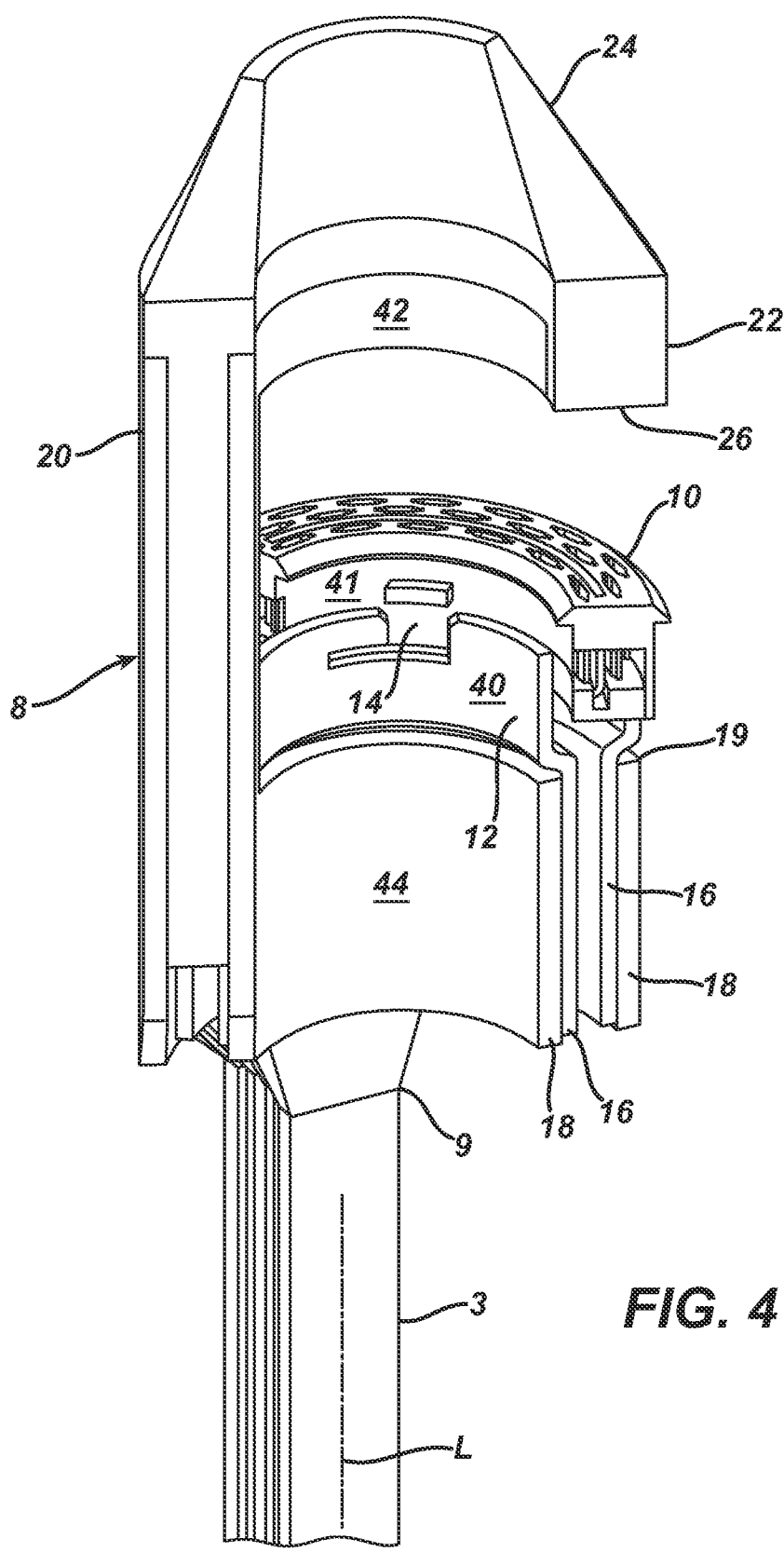
Figure 5:
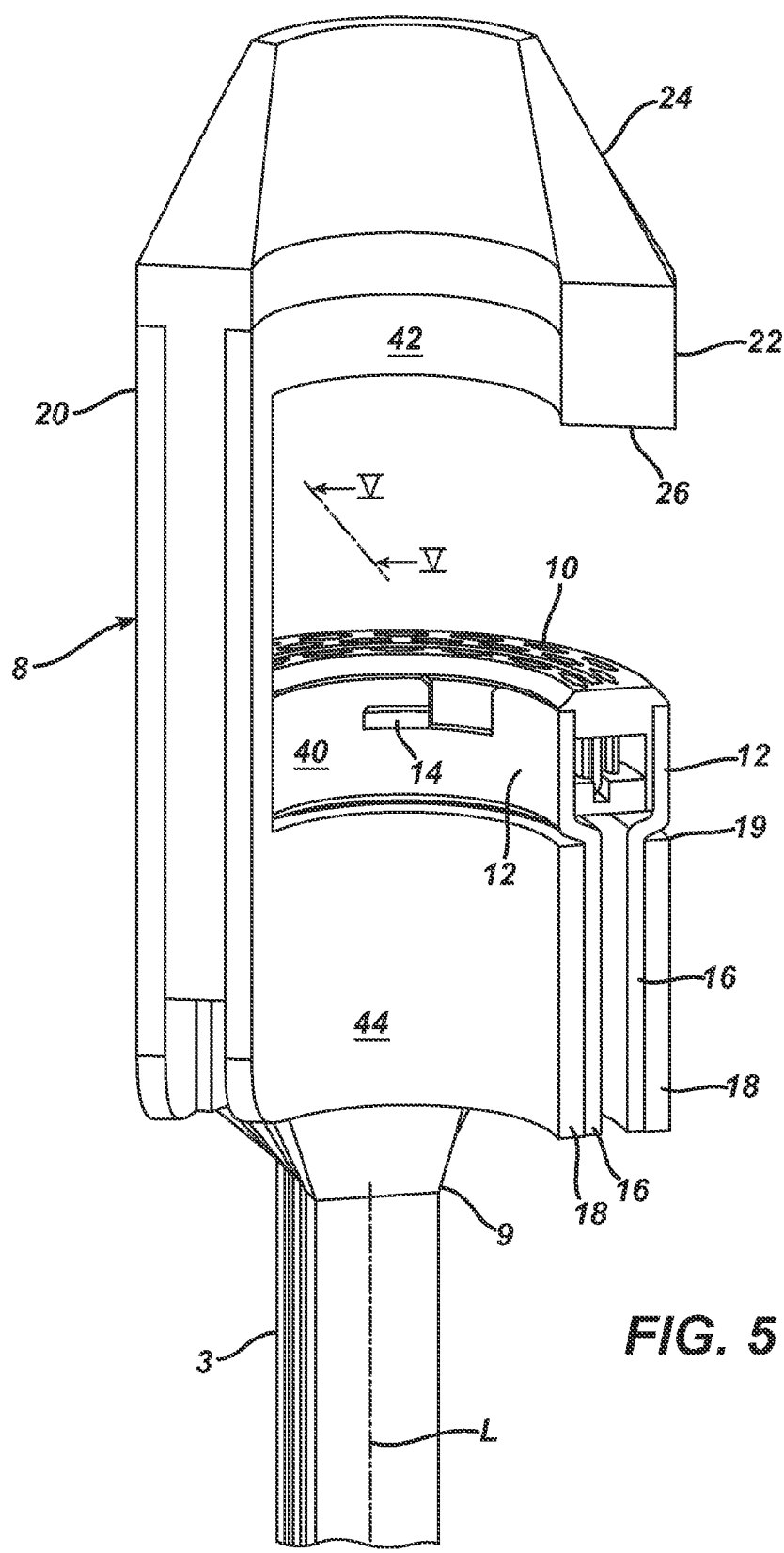

FIG. 4 is a magnified view of the staple fastening assembly 8. It includes a curved cartridge 10 which has an arc-like shape in the cross-sectional plane, the arc extending over an angle of about 180° in the embodiment. The cartridge 10 can be removed from the rest of the staple fastening assembly 8 and is mounted in a cartridge holder 12 by means of a bayonet locking 14. In FIG. 4, the cartridge 10 is shown in an unlocked state, slightly pulled out of the cartridge holder 12. The cartridge holder 12 is matched to the arc-like shape of the cartridge 10 in the cross-sectional plane and extends over an arc angle of about 180° as well. In FIG. 5, the cartridge 10 has been fully inserted into the cartridge holder 12 and is locked in the bayonet locking 14.

The proximal portion of the cartridge holder 12 is designed as a slider 16 which is narrower (seen in radial direction) than the distal portion of the cartridge holder 12. The slider 16 is slidably mounted in a guide portion 18, as is evident from FIGS. 4 and 5. By shifting the slider 16 inside the guide portion 18, the cartridge holder 12 including the cartridge 10 can be moved in the direction of the longitudinal axis L of the shaft 3. FIGS. 1 and 5 display a spaced position, when the shoulder of the cartridge holder 12 comes in close proximity to the distal end 19 of the guide portion 18.

The outer periphery of the guide portion 18 is similar to that of the distal portion of the cartridge holder 12, but because of an arm 20, its angle of arc is slightly larger than that of the cartridge 10. The arm 20 is rigidly connected to one end of the guide portion 18 and runs in parallel to the longitudinal axis L. It supports an anvil 22 having an atraumatically shaped distal end region 24 and a staple forming plane or surface 26, see FIG. 6. In the embodiment, the staple forming plane 26 is arranged at an angle of 90° with respect to the longitudinal axis L of the shaft 3. However, different transversal angles are conceivable as well. Moreover, it is possible to imagine the use of two arms to support the anvil, e.g., one arm at each of both ends of the guide portion.

Figure 6:
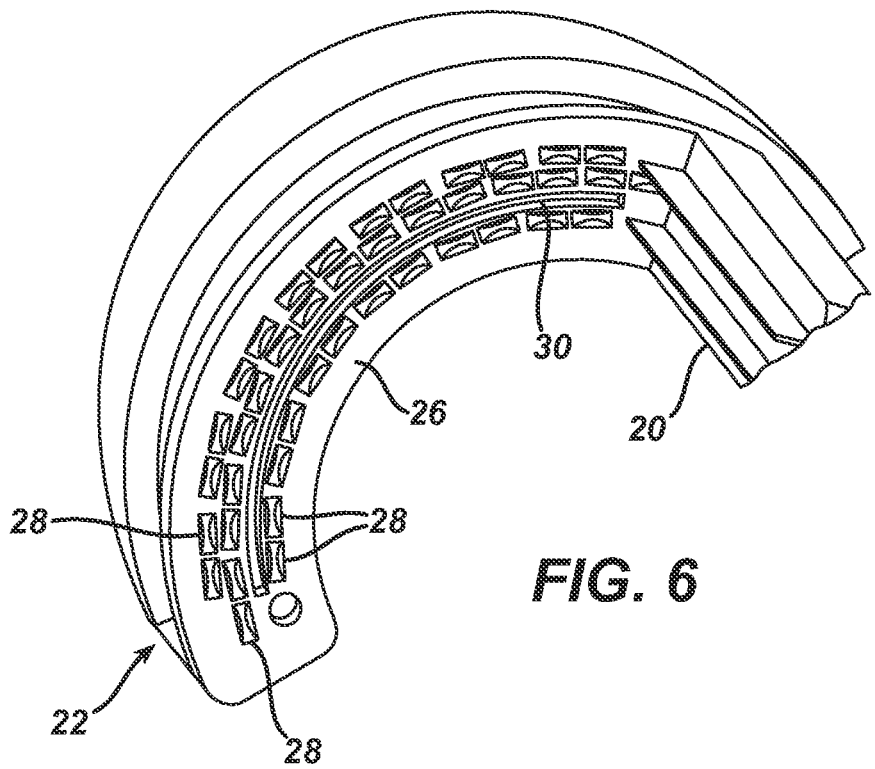

As shown in FIG. 6, the staple forming plane 26 of anvil 22 includes a plurality of staple forming depressions 28, which are arranged in three curved or arc-like open rows. In between the innermost row and the middle row, there is a continuous arc-like depression 30 for accommodating the end of an arc-like knife (see below).

Figure 7:
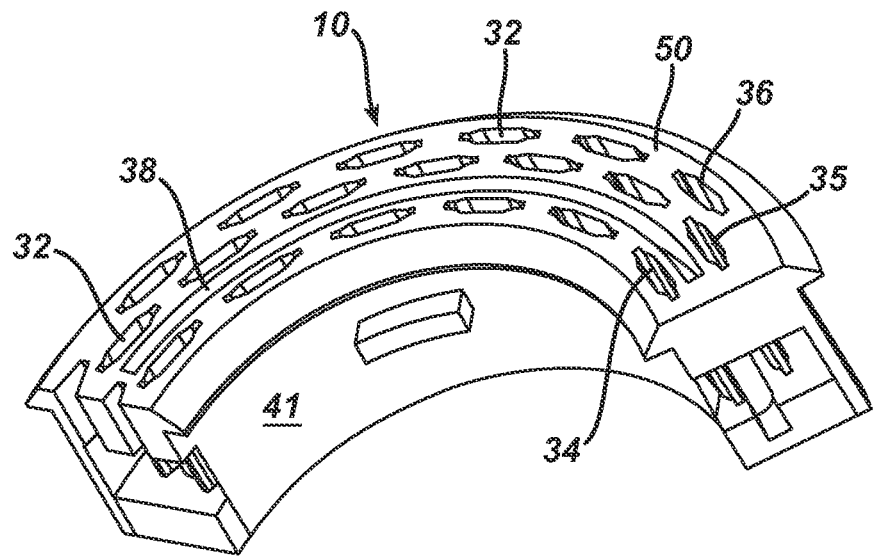

As illustrated in FIG. 7, the cartridge 10 is provided with a plurality of slots 32 which are arranged for cooperation with the staple forming depressions 28 and run in three curved or arc-like open rows 34, 35, and 36. A knife guide 38, which is aligned to the knife depression 30 in the mounted state of the cartridge 10, is visible in between rows 34 and 35.

Figure 8:
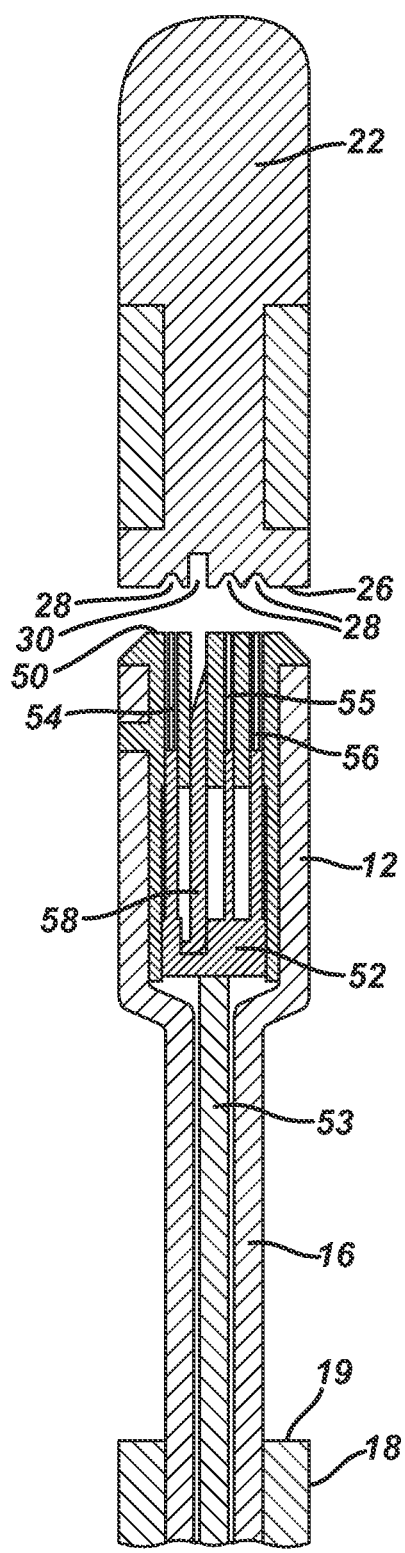
Figure 9:
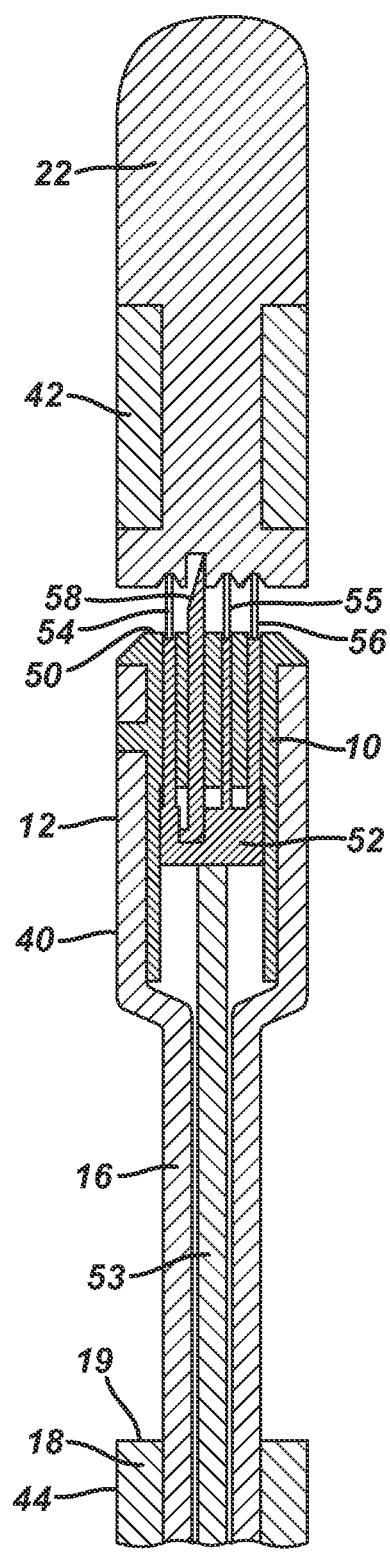

Before continuing with the description of the details of staple fastening assembly 8 by means of FIGS. 8 and 9, the overall geometry of the staple fastening assembly 8 is emphasized once again. Because of the generally arc-like shape (in the cross-sectional plane) of the guide portion 18, the cartridge holder 12, the cartridge 10, as well as the anvil 22 and the arrangement of the arm 20, the staple fastening assembly 8 allows a free and unobstructed access towards the concave inner faces 40 of the cartridge holder 12 (and thus towards the concave inner face 41 of the cartridge 10), 42 of the anvil 22 and 44 of the guide portion 18, see FIG. 5. Consequently, tissue in the area of the gap between the cartridge 10 and the anvil 22, when the cartridge 10 is in the spaced or open position as shown in FIG. 5, can be easily accessed and manipulated by means of separate surgical instruments.

FIGS. 8 and 9 are sectional views of the staple fastening assembly 8 along the line V-V of FIG. 5. FIG. 8 illustrates how the slider 16 of the cartridge holder 12 is guided inside the guide portion 18, which enables a longitudinal movement of the cartridge holder 12 including the cartridge 10. In this way, by actuating lever 5, the cartridge 10 can be moved towards the anvil 22 from the open position shown in FIGS. 1 and 5 to a closed position as shown in FIGS. 2 and 8. A mechanism for effecting this movement by means of the lever 5 is described, e.g., in U.S. Pat. No. 5,605,272. During the movement, the cartridge 10 maintains its parallel relationship with respect to the staple forming plane 26 of anvil 22.

In the closed position, tissue can be clamped in between the cartridge 10 and the anvil 22. It is advantageous, when the residual gap between the distal end of cartridge 10 and the staple forming plane 26 can be adjusted in order to prevent the tissue from being excessively compressed. Details on the mechanism of an adjustment device can be found, e.g., in U.S. Pat. No. 4,527,724. As an alternative to an adjustment device in the mechanism of the instrument, it is possible to use a set of cartridges in which each cartridge is designed for a different residual gap. This can be achieved, e.g., by different thicknesses (i e dimensions along the direction of the longitudinal axis L) of the distal section of a guide 50 (see next paragraph).

As shown in FIGS. 7 and 8, the cartridge 10 comprises a guide 50 provided with the slots 32 and the knife guide 38. At its proximal or bottom side, the cartridge 10 is open so that a pusher 52 can be shifted by means of a bar 53 which is guided inside the slider 16. The pusher 52 holds staples 54, 55, and 56, i.e. the staples of the rows 34, 35, and 36, as well as an arc-like knife 58.

When the trigger 6 is actuated by drawing it towards the handle 4 (see FIG. 3), the bar 53 and the pusher 52 are moved in distal direction, see FIG. 9. In this way, the staples 54, 55, and 56 are expelled from the cartridge 10. Moreover, the knife 58 is moved in distal direction as well. Since the distal edge of the knife 58 runs behind the pointed ends of the staples 54, 55, 56 (see FIG. 8), the knife 58 reaches the tissue clamped in between the cartridge 10 and the anvil 22 after the staples 54, 55, 56 have penetrated the tissue. This prevents the tissue from being displaced during the cutting process. After the knife 58 has cut the tissue, the excised tissue specimen contains the row 34 of staples 54, whereas the tissue remaining in the patient is held approximated by two rows 35, 36 of staggered staples 55, 56.

An embodiment of a possible mechanism for achieving the movement of bar 53 when the trigger 6 is actuated, is described in U.S. Pat. No. 5,605,272. This document also discloses some safety features which prevent the instrument 1 from being actuated or fired accidentally.

Figure 10:
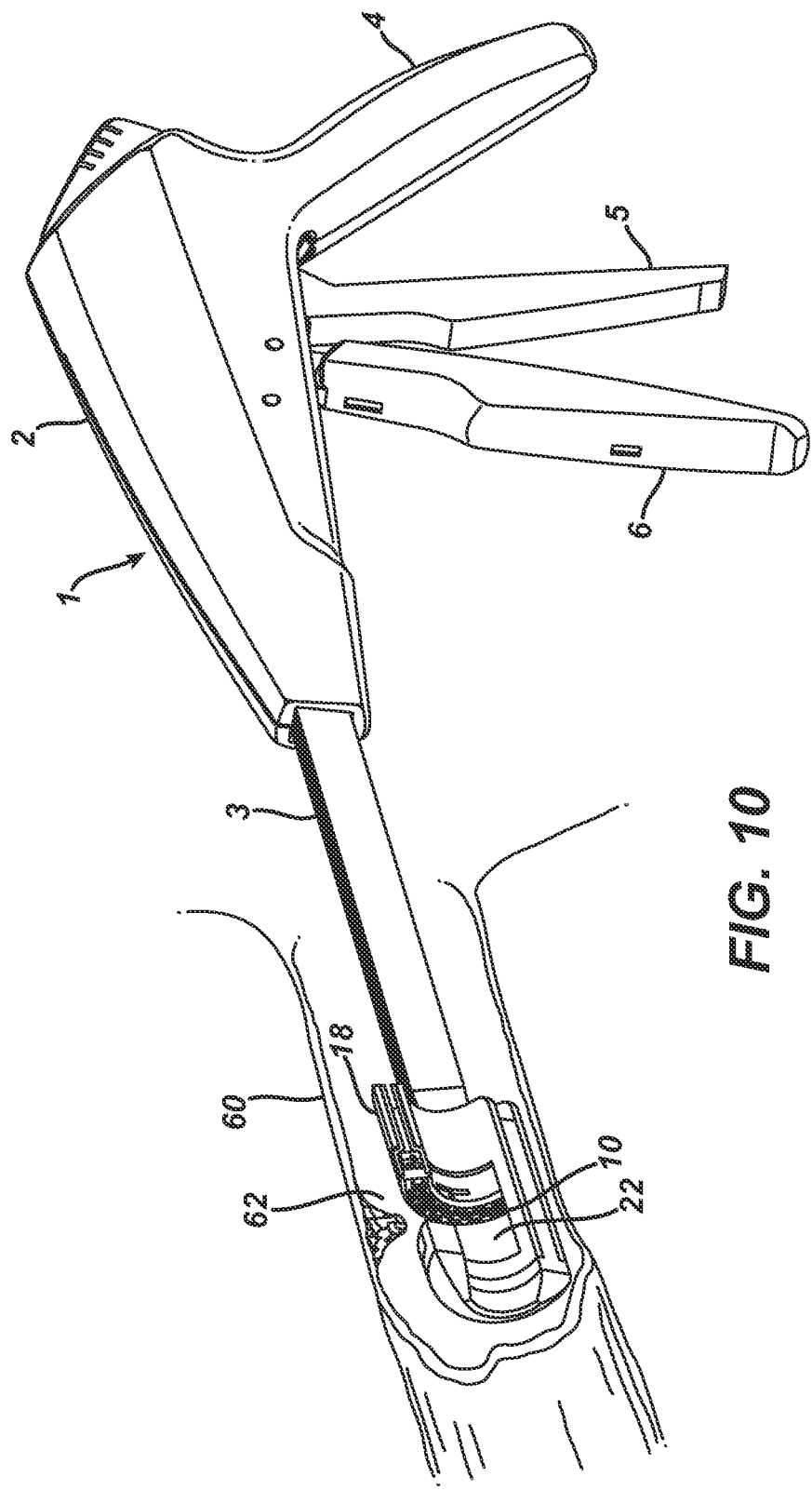

FIG. 10 illustrates in a schematic way how the instrument 1 can be used in order to resect a polyp 62 from a patient's rectum 60. The instrument 1 is inserted via the anal canal, the cartridge 10 being in the spaced or open position with respect to the anvil 22, as shown in FIG. 10. Now the polyp, or more precisely, healthy tissue in the area surrounding the polyp, can be pulled into the gap between the cartridge 10 and the anvil 22 by means of a separate surgical gripping instrument or traction sutures previously applied. This procedure is greatly facilitated by the curved shape of the guide portion 18, the cartridge 10, and the anvil 22 as well as the small cross-sectional area of the shaft 3, as already explained above. A separate endoscopic optical system can be helpful, but is not required. After the polyp has been secured, the cartridge 10 is moved towards the anvil 22 up to the closed position in order to clamp the tissue, as described above. Afterwards, the instrument 1 is fired, i.e. the trigger 6 is actuated which causes the staples to be expelled and the knife 58 to cut the tissue. The pointed ends of the staples are bent by the anvil 22. When the instrument 1 is retracted from the patient, the excised polyp 62 including the row 34 of staples is removed together with the staple fastening assembly 8 for pathological examination.

Other surgical procedures using the instrument 1 as well as the advantages thereof have already been mentioned in the introductory part of the description.

In special embodiments, the radius of curvature (e.g., of the cartridge, the cartridge holder, the open row(s) of staples, the knife, and/or the anvil) can be large or very large, up to infinite.

The invention claimed is:

1. A surgical stapling instrument comprising:
   a frame having a body portion and a handle extending from said body portion in a proximal end region of said instrument,
   a staple fastening assembly in a distal end region of said instrument, said staple fastening assembly including a curved cartridge, which comprises at least one curved open row of staples, and, at the distal end of said instrument, a curved anvil, which is adapted to cooperate with said cartridge for forming ends of the staples exiting from said cartridge,
   a staple forming plane of said anvil being arranged transversally with respect to a longitudinal axis of said body portion of said instrument,
   said staple fastening assembly being adapted to allow unobstructed access towards concave inner faces of said cartridge and of said anvil,
   a cartridge moving device, comprising a cartridge holder, adapted to move said cartridge essentially in parallel relationship towards said anvil from a spaced position for positioning tissue therebetween to a closed position for clamping tissue, said cartridge holder having a proximal portion which is narrower in a radial direction than a distal portion of the cartridge holder, and a staple driving device adapted to drive the staples out of said cartridge towards said anvil.

\* \* \* \* \*